(12) United States Patent
Iwamoto et al.

(10) Patent No.: US 11,619,616 B2
(45) Date of Patent: Apr. 4, 2023

(54) METHOD FOR QUANTIFYING MONOCLONAL ANTIBODY HAVING ANTIGEN OR ANTI-ANTIBODY BONDED THERETO

(71) Applicant: Shimadzu Corporation, Kyoto (JP)

(72) Inventors: Noriko Iwamoto, Kyoto (JP); Takashi Shimada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 611 days.

(21) Appl. No.: 16/624,193

(22) PCT Filed: Jun. 22, 2017

(86) PCT No.: PCT/JP2017/023034
§ 371 (c)(1),
(2) Date: Dec. 18, 2019

(87) PCT Pub. No.: WO2018/235228
PCT Pub. Date: Dec. 27, 2018

(65) Prior Publication Data
US 2020/0173960 A1    Jun. 4, 2020

(51) Int. Cl.
*G01N 30/72* (2006.01)
*G01N 33/68* (2006.01)
*C12Q 1/37* (2006.01)
*G01N 30/88* (2006.01)

(52) U.S. Cl.
CPC .......... *G01N 30/7233* (2013.01); *C12Q 1/37* (2013.01); *G01N 33/6848* (2013.01); *G01N 33/6857* (2013.01); *G01N 2030/8818* (2013.01); *G01N 2333/976* (2013.01); *G01N 2560/00* (2013.01); *G01N 2800/52* (2013.01)

(58) Field of Classification Search
CPC .......... G01N 30/7233; G01N 33/6848; G01N 33/6857; G01N 2030/8818; G01N 2333/976; G01N 2560/00; G01N 2800/52; G01N 2030/8831; G01N 33/6854; C12Q 1/37; C12Q 1/34
See application file for complete search history.

(56) References Cited

U.S. PATENT DOCUMENTS

| | | | | |
|---|---|---|---|---|
| 11,209,392 | B2 * | 12/2021 | Shimada | H01J 49/30 |
| 2016/0252522 | A1 | 9/2016 | Shimada et al. | |
| 2018/0059074 | A1 | 3/2018 | Shimada et al. | |
| 2020/0309735 | A1 * | 10/2020 | Shimada | H01J 49/30 |
| 2021/0003587 | A1 * | 1/2021 | Iwamoto | G01N 33/6857 |
| 2021/0215690 | A1 * | 7/2021 | Shimada | G01N 33/6854 |

FOREIGN PATENT DOCUMENTS

| | | |
|---|---|---|
| WO | 2015/033479 A1 | 3/2015 |
| WO | 2016/143224 A1 | 9/2016 |

OTHER PUBLICATIONS

Iwamoto et al., "Development of LCMS-Based Fully Validated Bioanalysis of CDR Peptides in Antibody Drugs by Fab-Selective Proteolysis: nSMOL Protocol," 2016 AAPS Annual Meeting and Exposition Poster, (2016).
Baker et al., "Immunogenicity of protein therapeutics: The key causes, consequences and challenges," 1 (4): 314-322 (2010).
Sasaki, "Clinical Application of Autoantibody Idiotypes," The Japanese Journal of Clinical Pathology, 42 (9): 925-928 (1994) (see partial English translation).
Ministry of Health, Labour and Welfare, "Preclinical Safety Evaluation of Biotechology-derived Pharmaceuticals," Mar. 23, 2012 (see partial English translation).
Ewles et al., "LC-MS/MS strategies for therapeutic antibodies and investigation into the quantitative impact of antidrug-antibodies," Bioanalysis, 8 (24): 2565-2579 (2016).
Written Opinion issued in corresponding International Patent Application No. PCT/JP2017/023034 dated Aug. 22, 2017 (see partial English translation).
International Search Report issued in corresponding International Patent Application No. PCT/JP2017/023034 dated Aug. 22, 2017.
Iwamoto et al., "Selective detection of complementarity-determining regions of monoclonal antibody by limiting protease access to the substrate: nano-surface and molecular-orientation limited proteolysis," Analyst, 139: 576-580 (2014).
Iwamoto et al., "The development of the validated LCMS bioanalysis of trastuzumab in human plasma using a selective detection method for complementarity-determining regions of monoclonal antibodies: nano-surface and molecular-orientation limited (nSMOL) proteolysis," Analytical Methods, 21: 9177-9183 (2015).
Iwamoto et al., "Fully validated LCMS bioanalysis of Bevacizumab in human plasma using nano-surface and molecular-orientation limited (nSMOL) proteolysis," Drug Metabolism and Pharmacokinetics, 31: 46-50 (2016).
Iwamoto et al., "Application of nano-surface and molecular-orientation limited proteolysis to LC-MS bioanalysis of cetuximab," Bioanalysis, 8 (10): 1009-1020 (2016).
Iwamoto et al., "Validated LC/MS Bioanalysis of Rituximab CDR Peptides Using Nano-surface and Molecular-Orientation Limited (nSMOL) Proteolysis," Biological and Pharmaceutical Bulletin, 39 (7): 1187-1194 (2016).
Iwamoto et al., "Validated LC-MS analysis of immune checkpoint inhibitor Nivolumab in human plasma using a Fab peptide selective quantitation method: nano-surface and molecular-orientation limited (nSMOL) proteolysis," Journal of Chromatography B, 1023-1024: 9-16 (2016).

(Continued)

*Primary Examiner* — Marcela M Cordero Garcia
(74) *Attorney, Agent, or Firm* — Morgan, Lewis & Bockius LLP

(57) ABSTRACT

The present invention provides a method in which a porous body having a monoclonal antibody to be measured immobilized in pores thereof is brought into contact with nanoparticles having a protease immobilized thereonto in a liquid to perform selective protease digestion of the monoclonal antibody and a peptide fragment obtained by the digestion is detected by liquid chromatography mass spectrometry (LC-MS), wherein the monoclonal antibody is digested with the protease in the presence of an antibody specifically binding to the monoclonal antibody or a target molecule of the monoclonal antibody.

20 Claims, No Drawings

Specification includes a Sequence Listing.

(56) References Cited

OTHER PUBLICATIONS

Iwamoto et al., "Multiplex LCMS Bioanalysis of Brentuximab Vedotin, Rituximab and Cetuximab towards Therapeutic Drug Monitoring Application by Combined Calibration Curve Using Fab-Selective Limited Proteolysis nSMOL," Clinical Pharmacology & Biopharmaceutics, 5 (4): 1000164 (2016).

Jenkins et al., "Recommendations for Validation of LC-MS/MS Bioanalytical Methods for Protein Biotherapeutics," The AAPS Journal, 17 (1) 1-16 (2015).

Baker et al., "Immunogenicity of protein therapeutics: The key causes, consequences and challenges," Self-Nonself, 1 (4): 314-322 (2010).

Ministry of Health, Labour and Welfare Iyaku Shokuhin Kyoku, "Preclinical Safety Evaluation of Biotechology-derived Pharmaceuticals," Mar. 23, 2012 (see partial English translation).

\* cited by examiner

```
                        SEQUENCE LISTING

<160> NUMBER OF SEQ ID NOS: 7

<210> SEQ ID NO 1
<211> LENGTH: 9
<212> TYPE: PRT
<213> ORGANISM: Artificial
<220> FEATURE:
<223> OTHER INFORMATION: Trastuzumab signature peptide

<400> SEQUENCE: 1

Ile Tyr Pro Thr Asn Gly Tyr Thr Arg
1               5

<210> SEQ ID NO 2
<211> LENGTH: 9
<212> TYPE: PRT
<213> ORGANISM: Artificial
<220> FEATURE:
<223> OTHER INFORMATION: Trastuzumab signature peptide

<400> SEQUENCE: 2

Phe Thr Ile Ser Ala Asp Thr Ser Lys
1               5

<210> SEQ ID NO 3
<211> LENGTH: 7
<212> TYPE: PRT
<213> ORGANISM: Artificial
<220> FEATURE:
<223> OTHER INFORMATION: Trastuzumab signature peptide

<400> SEQUENCE: 3

Gly Leu Glu Trp Val Ala Arg
1               5

<210> SEQ ID NO 4
<211> LENGTH: 11
<212> TYPE: PRT
<213> ORGANISM: Artificial
<220> FEATURE:
<223> OTHER INFORMATION: Trastuzumab signature peptide

<400> SEQUENCE: 4

Asn Thr Ala Tyr Leu Gln Met Asn Ser Leu Arg
1               5                   10
```

```
<210> SEQ ID NO 5
<211> LENGTH: 11
<212> TYPE: PRT
<213> ORGANISM: Artificial
<220> FEATURE:
<223> OTHER INFORMATION: Bevacizumab signature peptide

<400> SEQUENCE: 5

Ser Thr Ala Tyr Leu Gln Met Asn Ser Leu Arg
1               5                   10

<210> SEQ ID NO 6
<211> LENGTH: 9
<212> TYPE: PRT
<213> ORGANISM: Artificial
<220> FEATURE:
<223> OTHER INFORMATION: Bevacizumab signature peptide

<400> SEQUENCE: 6

Phe Thr Phe Ser Leu Asp Thr Ser Lys
1               5

<210> SEQ ID NO 7
<211> LENGTH: 16
<212> TYPE: PRT
<213> ORGANISM: Artificial
<220> FEATURE:
<223> OTHER INFORMATION: Bevacizumab signature peptide

<400> SEQUENCE: 7

Val Leu Ile Tyr Phe Thr Ser Ser Leu His Ser Gly Val Pro Ser Arg
1               5                   10                  15
```

METHOD FOR QUANTIFYING MONOCLONAL ANTIBODY HAVING ANTIGEN OR ANTI-ANTIBODY BONDED THERETO

SEQUENCE LISTING SUBMISSION VIA EFS-WEB

A computer readable text file, entitled "SequenceListing.txt" created on or about Dec. 18, 2019 with a file size of about 2 kb contains the sequence listing for this application and is hereby incorporated by reference in its entirety.

TECHNICAL FIELD

The present invention relates to a method for quantifying a monoclonal antibody and, more specifically, to a method for quantifying a monoclonal antibody in the presence of an antibody which specifically binds to the monoclonal antibody or a target molecule for the monoclonal antibody and an antigen. The present invention also relates to a method for evaluating the effectiveness of a treatment by a monoclonal antibody and the pharmaceutical characteristics based on a result of quantifying the monoclonal antibody after administration of the monoclonal antibody as an antibody pharmaceutical.

BACKGROUND ART

Recently, antibody pharmaceuticals have been developed for treatment of various disorders and clinically used. For example, trastuzumab known as an anti-cancer therapeutic agent is a humanized monoclonal antibody that can exhibit the anti-tumor effect by specifically binding to the HER2 protein expressed at high level in breast cancer or the like.

As one indicator of the effectiveness of an antibody pharmaceutical, blood concentration after administration can be employed as an important index. As such, following the kinetics of an antibody pharmaceutical after administration is very important for determining the effectiveness or pharmaceutical effect and considering the therapeutic plan thereafter.

Conventionally, the ELISA method has been mainly used as a method for quantification of an antibody pharmaceutical in blood, and ELISA kits with various constitutions are commercially available and used. However, due to the diversity of structure of an antibody pharmaceutical or the inhibition caused by modification of an antibody pharmaceutical in living body or binding of an autoantibody or the like, a problem occurs in that accurate quantification values may not be measured in the ELISA method.

Meanwhile, bioanalysis of an antibody pharmaceutical using LC-MS/MS method is actively developed in recent years as a quantification method for substituting the ELISA method. Unlike the ELISA method, and the LC-MS/MS method does not require the preparation of a detection antibody for an antibody pharmaceutical and allows direct measurement of an antibody pharmaceutical to be analyzed. Thus, a simple and universal quantification analysis can be performed so that it can be applied quickly for the analysis of an antibody pharmaceutical in development stage. Furthermore, it is indicated that, because the quantification of an antibody pharmaceutical based on LC-MS/MS analysis is not a method via an antigen antibody reaction like ELISA method but a technique by which molecules as a direct measurement subject or peptide fragments obtained by trypsin digestion are analyzed, the influence on quantification values by competition in blood, which is a hurdle for measurement by the ELISA method may be prevented. In the LC-MS/MS analysis, it is necessary to prevent incorporation of peptides, proteins, or hardly-volatile materials other than the substances to be measured in a sample provided for the analysis, to ensure the reproducibility and reliability of quantification values.

For the purpose of specific detection and quantification of a monoclonal antibody by mass spectrometry, the group of the inventors of the present invention studied for obtaining a peptide that is unique for an individual monoclonal antibody, and, as a result, has succeeded in achieving protease digestion by position selective solid phase-solid phase reaction of a monoclonal activity according to immobilization of both the monoclonal antibody and a protease that can digest the monoclonal antibody as a substrate in solid phase (Patent Literature 1 and Non Patent Literature 1). This method is a pre-treatment method for mass spectrometry in which a porous body having a monoclonal antibody as a measurement subject immobilized in pores thereof is brought into contact with nanoparticles having a protease immobilized thereonto in a liquid to perform selective protease digestion of the monoclonal antibody, and it is a breakthrough technique for having effective detection of the obtained peptide fragment by liquid chromatography mass spectrometry (LC-MS) analysis. The inventors named this method "nano-surface and molecular-orientation limited proteolysis method (nSMOL method)."

According to the quantification of an antibody pharmaceutical in blood by the nSMOL method, only a Fab region having a specific sequence of an antibody pharmaceutical is limitedly digested by trypsin and the ion suppression effect, which is the biggest problem of LC-MS/MS analysis, is inhibited, and thus this method can provide quantification values with higher stability and higher reliability.

The inventors of the present invention have already confirmed that, for measurement of blood concentration of about ten or more kinds of an antibody pharmaceutical, the method for detecting a monoclonal antibody using the nSMOL method and LC-MS/MS method in combination satisfies the requirements of the guidelines for validation of a method for biological analysis in Japan, USA, and Europe (Non Patent Literatures 2 to 7).

According to the guidelines, it is necessary to confirm all of the ability for selecting a molecule from interfering peaks, lower limit of quantification, calibratable range, data accuracy and precision, matrix effect from co-existing molecules, carry-over affecting the subsequent analysis, dilution integrity of a sample with high concentration, sample storage stability, and stability after sample treatment, and the reference values thereof are required to be ±20% or less for the lower limit of quantification, or ±15% or less for others (Non Patent Literature 8).

CITATION LIST

Patent Literature

Patent Literature 1: WO 2015/033479 A

Non Patent Literature

Non Patent Literature 1: Analyst. 2014 Feb. 7; 139(3): 576-80. DOI: 10.1039/c3an02104a Non Patent Literature 2: Anal. Methods, 2015; 21: 9177-9183

Non Patent Literature 3: Drug Metabolism and Pharmacokinetics, 2016; 31: 46-50

Non Patent Literature 4: Bioanalysis. 2016; 8(10):1009-20. doi: 10.4155. bio-2016-0018

Non Patent Literature 5: Biol Pharm Bull, 2016; 39(7):1187-94. doi: 10.1248/bpb.b16-00230

Non Patent Literature 6: J Chromatogr B Analyt Technol Biomed Life Sci; 2016; 1023-1024:9-16. doi: 10.1016/j.jchromb.2016.04.038

Non Patent Literature 7: Clin Pharmacol Biopharm 2016; 5:164. doi: 10.4172/2167-065X.1000164

Non Patent Literature 8: The AAPS Journal, 2015; 17(1): 1-16. doi:10.1208/s12248-014-9685-5

SUMMARY OF INVENTION

Technical Problem

When an antibody pharmaceutical is administered to a patient, while the pharmaceutical effect is exhibited as the antibody pharmaceutical binds to an antigen as a target molecule, there is a case in which an antibody against the antibody pharmaceutical, that is, anti-drug antibody (ADA, also referred to as an anti-antibody), is generated due to long-term administration. As such, in blood of a patient, the antibody pharmaceutical may be present in a state in which it binds to a target molecule and/or an ADA. While various types of antibody pharmaceuticals have been developed and used, it is found that there are pharmaceuticals which often show the generation of such ADAs in relatively short period and also other pharmaceuticals which do not generate ADAs in such amount even after administration for long period. Generation of ADAs is also different among individual patients, and it may also be different depending on the state of a patient. Upon binding to an ADA, the administered antibody pharmaceutical would be removed from a living body, and thus, in addition to evaluation of the binding to a target molecule, evaluation of the binding between the antibody pharmaceutical and an ADA generated in body of a patient, and detection of the antibody pharmaceutical in a state in which it is bound to a target molecule or an ADA, may provide very important information in evaluating the pharmaceutical effect of an antibody pharmaceutical. In order to quantify the blood concentration of an antibody pharmaceutical more accurately, it is necessary to consider the influence of the presence of such target molecule and ADA.

As described above, according to the quantification of a monoclonal antibody using an ELISA method, it is not possible to obtain accurate quantification values due to the presence of an ADA and a target molecule. Furthermore, as an ELISA kit, there is a kit in which a target molecule of an antibody pharmaceutical is immobilized in solid phase and an antibody recognizing the Fab region of human IgG is used as a detection antibody, a kit in which an anti-idiotype ADA is immobilized in solid phase and another ADA is used as a detection antibody, and the like. As a result, when an ADA or a target molecule binds to the antibody pharmaceutical to be detected, a deviation in measurement value may occur depending on the type of the ELISA kit used.

Meanwhile, although it has been proved that the nSMOL method is a pre-treatment method allowing very highly sensitive and very highly precise detection of a monoclonal antibody present in biological sample and application for measurement of blood concentration of various antibody pharmaceuticals, there are still unclarified points regarding the quantification of an antibody pharmaceutical bound to an ADA or a target molecule.

Solution to Problem

In consideration of the aforementioned problems, the inventors of the present invention have plural ADAs and target molecules as a ligand bound to an antibody pharmaceutical and carried out quantification based on LC-MS/MS analysis using the nSMOL method to figure out the influence exhibited in the measurement of an antibody pharmaceutical bound with ADA or target molecule by the nSMOL method.

As a result, it was indicated that, when an ADA having low dissociation rate constant (Kd value) is present as an anti-idiotype antibody at molar ratio of at least two times the antibody pharmaceutical, accuracy of the quantification value of a monoclonal body deteriorates in accordance with an increase in ADA concentration. It was also indicated that, when the ADA is not an anti-idiotype antibody or is an anti-idiotype antibody with high dissociation rate constant, there is no effect on the quantification analysis of a monoclonal antibody by the nSMOL method.

On the other hand, it becomes evident that, in the presence of a target molecule, an accurate quantification value is given even when the target molecule is present in an amount that is up to 100 times the monoclonal antibody.

Namely, the present invention provides the followings.

1. A method in which a porous body having a monoclonal antibody to be measured immobilized in pores thereof is brought into contact with nanoparticles having a protease immobilized thereonto in a liquid to perform selective protease digestion of the monoclonal antibody and a peptide fragment obtained by the digestion is detected by liquid chromatography mass spectrometry (LC-MS), wherein the monoclonal antibody is digested with the protease in the presence of an antibody specifically binding to the monoclonal antibody or a target molecule for the monoclonal antibody.

2. The method described in above 1, in which a part or all of the monoclonal antibody binds to the antibody specifically binding to the monoclonal antibody or the target molecule of the monoclonal antibody.

3. The method described in above 1 or 2, in which the monoclonal antibody is present in a biological sample in an amount of 1:1 or less in molecular ratio relative to the antibody specifically binding to the monoclonal antibody.

4. The method described in above 1 or 2, in which the monoclonal antibody is present in a biological sample in an amount of 1:100 or less relative to the target molecule.

5. The method described in any one of above 1 to 3, in which the monoclonal antibody is trastuzumab and an antibody specifically binding to trastuzumab is an anti-idiotype antibody.

6. The method described in any one of above 1 to 3, in which the monoclonal antibody is bevacizumab and an antibody specifically binding to bevacizumab is an anti-idiotype antibody.

7. A method for evaluation of effectiveness of a monoclonal antibody administered to a subject, comprising performing selective protease digestion of a monoclonal antibody by bringing a porous body having the monoclonal antibody in a biological sample derived from the subject immobilized in pores thereof into contact with nanoparticles having the protease immobilized thereonto in a liquid, calculating concentration of the monoclonal antibody in the biological sample by detecting a peptide fragment resulting from the digestion by liquid chromatography mass spectrometry (LC-MS), and determining the presence or absence and/or degree of influence on calculation result exhibited by existence of an antibody specifically binding to the monoclonal antibody.

8. The method described in above 7, in which the monoclonal antibody is trastuzumab and a peptide fragment having the amino acid sequence represented by SEQ ID NO: 1 to 4 is detected.

9. The method described in above 7, in which the monoclonal antibody is bevacizumab and a peptide fragment having the amino acid sequence represented by SEQ ID NO: 5 to 7 is detected.

Advantageous Effects of Invention

The method of the present invention allows highly sensitive and highly precise detection of a monoclonal antibody which is present with an ADA or a target molecule in a biological sample. Furthermore, according to the method of the present invention, it is possible to provide information that is useful in terms of the effectiveness of a treatment by an antibody pharmaceutical.

DESCRIPTION OF EMBODIMENTS

In one embodiment, the present invention provides a method in which a porous body having a monoclonal antibody to be measured immobilized in pores thereof is brought into contact with nanoparticles having a protease immobilized thereonto in a liquid to perform selective protease digestion of the monoclonal antibody and a peptide fragment obtained by the digestion is detected by liquid chromatography mass spectrometry (LC-MS), the monoclonal antibody being digested with the protease in the presence of an antibody specifically binding to the monoclonal antibody or a target molecule of the monoclonal antibody.

As described herein, the "subject" indicates mammals such as mouse, rat, rabbit, goat, cow, or human, and it is particularly a human. The monoclonal antibody to be measured is, more specifically, a monoclonal antibody which was administered to a subject, mainly to a human patient, and present in a biological sample derived from the subject. As described herein, the biological sample indicates a sample derived from blood or tissues of a subject, and preferably plasma, serum, or tissue homogenate extract. After being obtained from a patient or a subject, the biological sample can be provided immediately for the method of the present invention, but it can also be provided for the method of the present invention after storage at room temperature or low temperature.

According to the method of the present invention, concentration of the monoclonal antibody in a biological sample may be within a range of 0.05 to 300 µg/ml for each.

In order to detect and quantify a monoclonal antibody by mass spectrometry, it is necessary that those other than the substance to be measured are first removed as much as possible from a biological sample like blood or tissues, and then dissolution in a suitable solvent is made. Furthermore, because an antibody has molecular weight too large for direct analysis, it is degraded to peptides by a protease and then subjected to isolation by liquid chromatography followed by mass spectrometry. The molecular weight of a peptide suitable for the analysis is about 1000 to 3000 Da.

When a common protein molecule is degraded with a protease, about 100 peptide fragments are produced, and in the case of an antibody, much higher than 200 peptide fragments are produced. As such, just with a single protein, the number of fragments to be measured is very large. In the case of using a complex biological sample, a huge sample set is yielded so that the possibility of interference on individual analysis cannot be overlooked.

The nSMOL method developed by the present inventors can be used as a pre-treatment method of mass spectrometry by which a Fab region-selective peptide fragment effective for detection of a monoclonal antibody is produced.

<Summary of nSMOL Method>

The method of the present invention is carried out by applying the nSMOL method which has been previously developed by the group of the present inventors. Details of the nSMOL method are described in WO 2015/033479; and Iwamoto N et. al., Selective detection of complementarity-determining regions of monoclonal antibody by limiting protease access to the substrate: nano-surface and molecular-orientation limited proteolysis, Analyst. 2014 Feb. 7; 139(3): 576-80. DOI: 10.1039/c3an02104a, for example. Furthermore, with regard to the modified technique of the nSMOL method, descriptions are made in WO 2016/143223; WO 2016/143224; WO 2016/143226; WO 2016/143227; Iwamoto N et. al., Bioanalysis, doi: 10.4155/bio-2016-0018; and Iwamoto N et. al., Biological & Pharmaceutical Bulletin, 2016, doi:10.1248/bpb.b16-00230, or the like, for example. Disclosures of those documents are incorporated herein by reference.

More specifically, the nSMOL method is a method in which a porous body having a monoclonal antibody to be measured immobilized in pores thereof is brought into contact with nanoparticles having a protease immobilized thereonto in a liquid to perform selective protease digestion of the monoclonal antibody. The peptide obtained by the nSMOL method preferably has an amino acid sequence including amino acids originating from Fab region of an antibody, for example, amino acids originating from CDR1, CDR2, or CDR3 region of a heavy chain or a light chain.

<Antibody>

The monoclonal antibody to be measured in the method of the present invention is an immunoglobulin IgG in which an Fab domain and an Fc domain are linked to each other via a hinge, and two heavy chains and two light chains constituting an antibody molecule are each formed of a constant region and a variable region. The constant region has an amino acid sequence that is common to most of antibodies originating from the same species. On the other hand, in the variable region, there are three sites having specific sequence, so-called complementarity determining regions (CDRs). A three-dimensional structure defined by the CDR (CDR1, CDR2, and CDR3) regions is involved in specific binding with an antigen, and thereby, an antibody-antigen complex is formed.

Examples of the monoclonal antibody which may become a measurement subject for the method of the present invention include, although not limited thereto, a human antibody such as panitumumab, ofatumumab, golimumab, ipilimumab, nivolumab, ramucirumab, or adalimubab; a humanized antibody such as tocilizumab, trastuzumab, trastuzumab-DM1, bevacizumab, omalizumab, mepolizumab, gemtuzumab, palivizumab, ranivizumab, certolizumab, ocrelizumab, mogamulizumab, or eculizumab; and a chimeric antibody such as rituximab, cetuximab, infliximab, or basiliximab. Furthermore, the molecular diameter of the monoclonal antibody is about 14.5 nm.

Furthermore, a conjugate added with further functions while maintaining the specificity of a monoclonal antibody, for example, Fc fusion protein and antibody-drug conjugate (for example, brentuximab vedotin, gemtuzumab·ozogamicin, trastuzumab-emtansine, or the like), is also included in the monoclonal antibody to be measured in the method of the present invention. The conjugate may be dissociated prior to measurement and only an antibody part may be subjected to an analysis. Alternatively, the conjugate form itself may be subjected to an analysis. Based on the descriptions in the specification, a person skilled in the art can set the optimum conditions for the method of the present invention depending on the substance to be measured.

Trastuzumab, described herein as an exemplary monoclonal antibody, is a humanized monoclonal antibody that can specifically bind to HER2 protein, and it can be obtained under the trade name of Herceptin. The amino acid sequence information of trastuzumab can be obtained from Kyoto Encyclopedia of Genes and Genomes (KEGG), for example.

Furthermore, bevacizumab described herein as another exemplary monoclonal antibody is a humanized monoclonal antibody that can specifically bind to a vascular endothelial growth factor (VEGF), and it can be obtained under the trade name of Avastin. The amino acid sequence information of bevacizumab can also be obtained from Kyoto Encyclopedia of Genes and Genomes (KEGG), for example.

The method of the present invention using the nSMOL method is a method of directly measuring a peptide fragment derived from an antibody based on mass spectrometry of a peptide fragment obtained by selective protease digestion of Fab region of a monoclonal antibody. As such, the method of the present invention can be applied without depending on the type of an antibody, and, without being limited to the exemplary antibodies described above, it can also be applied to a newly developed monoclonal antibody or the like. Based on the disclosures of the research articles and the patent applications previously reported by the present inventors, and common technical knowledge relating to mass spectrometry, a person skilled in the art can obtain the information required for detecting a target antibody and select an appropriate signature peptide.

The present inventors found that the nSMOL method can provide a suitable quantification result of a target monoclonal antibody by protease digestion even in the presence of an antibody specifically binding to the monoclonal antibody or a target molecule for the monoclonal antibody, and can yield useful information in terms of the effectiveness of a treatment with an antibody pharmaceutical or the evaluation of a pharmaceutical effect. Namely, in the method of the present invention, a part or all of the monoclonal antibody may bind to an antibody specifically binding to the monoclonal antibody or a target molecule of the monoclonal antibody.

For example, even when the monoclonal antibody is present in a biological sample in an amount of 100:1, 10:1, 5:1, 1:1, 1:2, 1:5, 1:10, 1:50, or 1:100 or less in molecular ratio, for example, 1:1 or less relative to an antibody specifically binding to the monoclonal antibody, there is no influence exhibited on a quantification value of the monoclonal antibody.

Furthermore, even when the monoclonal antibody is present in a biological sample at 10:1, 5:1, 1:1, 1:5, 1:10, 1:50, or 1:100 or less relative to a target molecule, there is no influence exhibited on a quantification value of the monoclonal antibody.

In one embodiment of the present invention, the monoclonal antibody is trastuzumab, and the antibody specifically binding to trastuzumab can be an anti-idiotype antibody. Furthermore, in another embodiment, the monoclonal antibody is bevacizumab, and the antibody specifically binding to bevacizumab can be an anti-idiotype antibody.

<Porous Body>

The material of the porous body used for the method of the present invention is not particularly limited as long as the material has plural pores, and activated carbon, a porous membrane, porous resin beads, metal particles, or the like can be used. Among them, those capable of binding site-specifically to an antibody are particularly preferred.

The pore is not particularly limited in shape. Furthermore, like a porous membrane, those having pores which penetrate a porous body can also be used. Pore size of the porous body is not particularly limited, and it is preferably determined in consideration of the molecular diameter or the like of the antibody, so that the site to be selectively digested is located near the surface layer of the pores when the antibody is immobilized. The average pore diameter of the porous body is appropriately set to fall within the range of about 10 nm to 200 nm and to be smaller than the average particle diameter of the nanoparticles. The average pore diameter of the porous body is, for example, preferably about 20 nm to 200 nm, and more preferably about 30 nm to 150 nm. In order to immobilize the Fc domain of an antibody in the pores and to achieve site-selective protease digestion of the Fab domain, the pore diameter of the porous body is preferably 30 nm to 150 nm, more preferably 40 nm to 120 nm, and even more preferably 50 nm to 100 nm, in particular, about 100 nm.

According to the nSMOL method, a monoclonal antibody to be measured is immobilized in pores of a porous body. For this purpose, a porous body having a linker molecule that can site-specifically interact with an antibody immobilized in pores is preferably used. Examples of the interaction between the antibody and the linker molecule include chemical bond, hydrogen bond, ionic bond, complex formation, hydrophobic interaction, van der Waals interaction, electrostatic interaction, and stereospecific interaction.

As the linker molecule, Protein A, Protein G, or the like that can site-specifically bind to the Fc domain of an antibody is preferably used. By using a porous body having these linker molecules immobilized in the pores, the Fc domain of an antibody is immobilized in the pores and the Fab domain is located near the surface layer of the pores. Accordingly, as the orientation of an antibody in pores is controlled, and site-selective protease digestion of the Fab domain can be achieved.

The size of a linker molecule is selected such that a selective cleavage site of an antibody is located near a surface layer of the pores. The molecular size in a state in which a linker molecule and an antibody are bound to each other is preferably about 0.5 times to 1.5 times, more preferably about 0.6 times to 1.2 times, even more preferably about 0.7 times to 1.1 times, and particularly preferably about 0.8 times to 1 time the pore diameter of the porous body. Furthermore, when a linker molecule is not immobilized to a porous body and an antibody is directly bound in pores, it is preferable that a molecular diameter of the antibody and a pore diameter of the porous body satisfy the above relation.

Examples of the porous body that can be suitably used in the present invention include, although not particularly limited to, Protein G Ultralink resin (manufactured by Pierce Corporation), Toyopearl TSKgel (manufactured by Tosoh Corporation), Toyopearl AF-rProtein A HC-650F resin (manufactured by Tosoh Corporation), Protein A Sepharose (GE Healthcare), and KanCapA (KANEKA CORPORATION).

A method for immobilizing an antibody in pores of the porous body is not particularly limited, and an appropriate method can be adopted according to characteristics of the antibody, the porous body or a linker molecule and the like. For example, when an antibody is immobilized to a porous body in which Protein A or Protein G is immobilized in pores thereof, the antibody can be easily immobilized in the pores by mixing a suspension of the porous body with a solution containing the antibody.

A quantitative ratio of the porous body to an antibody can be appropriately set according to a purpose. For example, when a quantitative analysis of an antibody is performed, it is desirable that almost the entire antibody in a sample be immobilized to the porous body. Therefore, it is preferable that a quantitative ratio be set such that an amount of the porous body is excessive with respect to an estimated content of the antibody in the sample.

<Nanoparticles>

The nanoparticles are used for the purpose of immobilizing a protease on surfaces of the nanoparticles and controlling access of the protease to an antibody immobilized in pores of the porous body. Therefore, the nanoparticles have a larger average particle diameter than the average pore diameter of the porous body so as not to enter deep inside the pores of the porous body.

The nanoparticles are not particularly limited in shape. However, from a viewpoint of homogenization of access of the protease to the pores of the porous body, spherical nanoparticles are preferred. Furthermore, it is preferable that the nanoparticles have a high dispersion property and a uniform average particle diameter.

A material of the nanoparticles is not particularly limited as long as the above protease can be immobilized on surfaces of the nanoparticles. A metal, a resin, a silica gel, or the like can be appropriately used as the material of the nanoparticles. Furthermore, a metal having the surface coated with a resin, a resin having the surface coated with a metal, or the like can also be used.

As a type of the nanoparticles, magnetic nanoparticles that can be dispersed or suspended in an aqueous medium and can be easily recovered from the dispersion or suspension by magnetic separation or magnetic precipitation separation are preferable. Furthermore, from a viewpoint that aggregation is less likely to occur, magnetic nanoparticles coated with an organic polymer on the surfaces thereof are more preferable. Examples of base materials of magnetic nanoparticles include ferromagnetic alloys such as iron oxide (magnetite ($Fe_3O_4$), maghemite ($\gamma$-$Fe_2O_3$)), and ferrite ($Fe/M)_3O_4$. In the ferrite ($Fe/M)_3O_4$, M means a metal ion that can be used together with an iron ion to form a magnetic metal oxide, and typically, $Co^{2+}$, $Ni^{2+}$, $Mn^{2+}$, $Mg^{2+}$, $Cu^{2+}$, $Ni^{2+}$ and the like are used. Furthermore, examples of the organic polymer coating the magnetic nanoparticles may include polyglycidyl methacrylate (poly GMA), a copolymer of GMA and styrene, polymethyl methacrylate (PMMA), polymethyl acrylate (PMA), and the like. Specific examples of magnetic nanobeads coated with an organic polymer include FG beads, SG beads, Adembeads, nanomag, and the like. As a commercially available product, for example, FG beads (polymer magnetic nanoparticles having a particle diameter of about 200 nm obtained by coating ferrite particles with polyglycidyl methacrylate (poly GMA)) manufactured by Tamagawa Seiki Co., Ltd. is preferably used.

In order to suppress the adsorption of a nonspecific protein and to have selective immobilization of a protease, the nanoparticles may preferably be modified with a spacer molecule capable of binding to the protease. By immobilizing a protease via a spacer molecule, desorption of the protease from surfaces of the nanoparticles is suppressed, and site selectivity of protease digestion can be improved. Furthermore, by adjusting the molecular size of a spacer, it is possible to achieve selective access of the protease to desired location of an antibody, and thus the enhanced site selectivity can also be obtained.

A spacer molecule having the above molecular diameter and capable of immobilizing a protease is preferably a non-protein, and is preferably a molecule having a functional group at the terminus, and examples of the functional group include an amino group, a carboxyl group, an ester group, an epoxy group, a tosyl group, a hydroxyl group, a thiol group, an aldehyde group, a maleimide group, a succinimide group, an azide group, a biotin, an avidin, and a chelate. For example, for immobilization of a trypsin, a spacer molecule having an activated ester group is preferred. Furthermore, as a spacer arm portion other than the functional group in the spacer molecule, a hydrophilic molecule can be used, and examples thereof include polyethylene glycol and its derivatives, polypropylene glycol and its derivatives, polyacrylamide and its derivatives, polyethyleneimine and its derivatives, poly(ethylene oxide) and its derivatives, poly(ethylene terephthalic acid) and its derivatives, and the like.

Nanoparticles that are surface-modified with such spacer molecule are also commercially available, and those commercially available nanoparticles may be suitably used. For example, nanoparticles modified with a spacer molecule having an ester group (active ester group), which is activated with N-hydroxysuccinimide, are commercially available under the trade name "FG beads NHS" (Tamagawa Seiki Co., Ltd.). The FG beads NHS has a particle diameter of about 200 nm±20 nm, for example, 190 nm, and is very homogeneous as nanoparticles.

<Protease>

According to the nSMOL method, a protease can cleave an antibody immobilized in pores of a porous body at a specific amino acid sequence site and produce a peptide fragment including amino acids in Fab region. The peptide fragment may be a fragment having an amino acid sequence which includes amino acids originating from CDR2 region, for example.

The type of the protease to be immobilized on the nanoparticles may be suitably selected depending on the type of the monoclonal antibody to be quantified or identified by mass spectrometry, and examples thereof include, although not limited thereto, trypsin, chymotrypsin, lysyl endopeptidase, V8 protease, AspN protease (Asp-N), ArgC protease (Arg-C), papain, pepsin, and dipeptidyl peptidase. Two or more kinds of the proteases may be used in combination. Trypsin is particularly preferably used as a protease.

When a commercially available protease is used, it is preferable that a protease of mass spectrometry grade or of sequencing (sequence) grade is used. For example, as a trypsin of mass spectrometry grade, trypsin of which lysine residues are reductive-methylated to increase resistance to self-digestion is commercially available. Alternatively, depending on the type of a target monoclonal antibody, use of a crude protease, a protease without any treatment for resistance to self-digestion like reductive methylation, or a protease with trypsin activity and chymotrypsin activity may be preferred.

Examples of the protease which can be suitably used for protease digestion by the nSMOL method in the method of the present invention include Trypsin Gold (manufactured by Promega Corporation) and Trypsin TPCK-treated (manufactured by Sigma Aldrich).

<Immobilization of Protease onto Nanoparticles>

A method for immobilizing the protease on surfaces of nanoparticles is not particularly limited. An appropriate method can be adopted according to characteristics of the protease and the nanoparticles (or spacer molecules modifying the surfaces of the nanoparticles) or the like. For example, when the protease is immobilized on spacer-modified surfaces of the nanoparticles, by mixing a suspension of the nanoparticles with a solution containing the protease, the protease can be immobilized on the surfaces of the nanoparticles. A method of amine coupling of the nanoparticles and the protease via functional groups of the spacer molecule is preferable. For example, a carboxyl group modifying surfaces of nanoparticles can be esterified with N-hydroxysuccinimide (NHS) to form an activated ester group, to which an amino group of the protease can be bound. This coupling reaction can be performed in the presence of carbodiimide as a condensing agent, and examples of the carbodiimide include 1-ethyl-3-(3-dimethylaminopropyl) carbodiimide (EDAC), N,N'-dicyclohexyl-carbodiimide (DCC), bis(2,6-diisopropylphenyl) carbodiimide (DIPC), and the like. Furthermore, an amino group of the protease may be bound to an amino group modifying surfaces of nanoparticles using a cross-linking agent such as glutaraldehyde, bifunctional succinimide, bis(sulfosuccinimidyl) suberate (BS3), sulfonyl chloride, maleimide, and pyridyl disulfide.

The coupling method of the nanoparticles and the protease via the functional groups of the spacer molecule can be performed by a simple operation of adding a protease solution to a suspension of the nanoparticles and mixing and stirring the mixture under certain conditions.

After immobilizing the protease on the surface of the nanoparticles, the active part on surface of the nanoparticles, which does not bind to the protease, may preferably be inactivated. If there is a spacer molecule on the surface of the nanoparticles to which the protease is not immobilized, the non-bound spacer molecule may bind to impurities or the like in a sample, and thus yielding problems like a negative influence on the protease digestion or immobilization of a peptide fragment produced by the protease digestion on the nanoparticles. By blocking the non-bound spacer molecule after protease immobilization, these problems can be suppressed. As a method for inactivating the active part which does not bind to the protease, chemical modification is preferable. For example, an activated ester group can form an amide bond through a reaction with a primary amine to yield the inactivation.

Furthermore, FG beads Trypsin DART®, which are nanoparticles to which trypsin is immobilized as a protease, are included in pre-treatment kit for LC/MS/MS "nSMOL Antibody BA Kit" (SHIMADZU CORPORATION), and can be suitably used for the method of the present invention.

<Protease Digestion>

By bringing a porous body in which an antibody is immobilized and nanoparticles having a protease immobilized on the surface thereof into contact with each other in a liquid, the antibody is digested by the protease and peptide fragments are produced. Herein, the term "liquid" means that a substrate (solid phase) and an enzyme (solid phase) are in contact with each other in a liquid phase, and is also intended to mean an aqueous medium suitable for a protease digestion reaction.

Conditions of the protease digestion are not particularly limited, and conditions similar to general protease digestion can be suitably adopted. For example, it is preferable to incubate usually at a temperature of about 37° C. for about 1 hour to 20 hours in a buffer solution adjusted to a vicinity of an optimum pH of the protease. Alternatively, it is also possible to have incubation for 3 to 8 hours at about 50° C. under saturated vapor pressure.

A quantitative mixing ratio of the porous body in which an antibody is immobilized to the nanoparticles having a protease immobilized on the surface thereof is not particularly limited either, and it may be selected so as to have an amount of the protease corresponding to an amount of the antibody. The general condition for protease digestion is substrate:protease=about 100:1 to 20:1 (weight ratio). In contrast, in the present invention, access between the antibody and the protease is physically restricted by the combination of the porous body and the nanoparticles, and therefore, it is preferable to increase the amount of the protease as compared to general protease digestion. For example, antibody:protease ratio is preferably about 30:1 to 3:1, more preferably about 15:1 to 4:1, and even more preferably about 10:1 to 5:1.

More specifically, the C terminal side of an antibody is immobilized on Protein G resin with pore diameter of 100 nm, for example, and the variable region of the antibody is oriented to a solution side. Next, the protease is immobilized on the surface of the nanoparticles having particle diameter of 200 nm.

The protease digestion can be carried out under tapping rotation in which regular tapping is performed with stirring by mild rotation to the extent that uniform dispersion of the porous body and nanoparticles in a liquid is maintained, although it is not particularly limited thereto. "Mild rotation" means revolution number of about 3 to 10 rpm, for example, and "tapping" means instant motion like flicking or applying a shock (for example, frequency of 1 to 5 times, and preferably 2 to 4 times per minute). Accordingly, the porous body having an antibody immobilized thereon is effectively brought into contact with the nanoparticles having a protease immobilized thereonto while both of them are maintaining a dispersion state, and thus the efficiency of the protease digestion reaction can be enhanced.

As described above, since the contact between the monoclonal antibody as a substrate and the protease is limited by the method of the present invention, a peptide derived from the Fab region, which exhibits the specificity of the monoclonal antibody, is easily and effectively digested, and can be subjected to mass spectrometry.

<Removal of Porous Body and Nanoparticles>

To provide a target peptide fragment obtained by protease digestion to mass spectrometry, it is necessary to remove the porous body and nanoparticles. This can be achieved by subjecting a sample after the protease digestion to an operation like filtration, centrifugal separation, magnetic separation, dialysis, and the like.

When the porous body and nanoparticles are removed by filtration, pore diameter of a filtration membrane to be used is selected from a range which does not allow passage of the porous body and nanoparticles but allows passage of digested peptides. For example, by carrying out the filtration using a filtration membrane made of polyvinylidene fluoride (PVDF) (low-binding hydrophilic PVDF having a pore diameter of 0.2 μm, manufactured by Millipore Corporation), a filtration membrane made of polytetrafluoroethylene (PTFE) (low-binding hydrophilic PTFE having a pore diameter of 0.2 μm, manufactured by Millipore Corporation), or the like, the porous body and the nanoparticles can be easily removed. When the filtration is made by centrifugal filtration, rapid and easy filtration can be achieved.

<Liquid Chromatography Mass Spectrometry (LC-MS)>

According to LC-MS analysis of a sample containing the peptide fragment obtained above, identification or quantification of an antibody can be carried out.

For the purpose of more reliable separation of the peptide fragment and improved precision of analysis, a sample before being subjected to mass spectrometry may be separated and concentrated using liquid chromatography (LC). When separating a sample using LC, an eluate from LC may be directly ionized and subjected to mass spectrometry. Analysis can also be performed using LC/MS/MS or LC/MSn combining LC with tandem mass spectrometry. Furthermore, the eluate from LC may be fractionated once and then subjected to mass spectrometry. An LC column is not particularly limited, and a hydrophobic column such as C30, C18, C8, and C4 generally used in peptide analysis, a carrier for hydrophilic affinity chromatography, and the like can be appropriately selected and used.

Mass spectrometry can determine an amino acid sequence and thus can determine whether or not a peptide fragment is derived from a specific protein such as an antibody. Furthermore, based on peak intensity, concentration of the peptide fragment in a sample can be determined. In performing analysis, a sample may be subjected to treatments such as desalting, solubilization, extraction, concentration, and drying when necessary, and then used for the analysis.

The ionization method in mass spectrometry is not particularly limited, and an electron ionization (EI) method, a chemical ionization (CI) method, a field desorption (FD) method, a fast atom collision (FAB) method, a matrix assisted laser desorption ionization (MALDI) method, an electrospray ionization (ESI) method, and the like can be adopted. A method for analyzing an ionized sample is not particularly limited either, and a method of a magnetic field deflection type, a quadrupole (Q) type, an ion trap (IT) type, a time of flight (TOF) type, a Fourier transform ion cyclotron resonance (FT-ICR) type, or the like can be appropriately determined according to the ionization method. Furthermore, MS/MS analysis or multi-step mass spectrometry of MS3 or higher can also be performed using a triple quadrupole mass spectrometry analyzer or the like.

In recent years, a hybrid type mass spectrometry analyzer referred to as triple quadrupole is mainly used. According to the analyzer of this type, ionized biomolecules first pass through a portion referred to as octopole to have a smaller ion molecular vibration radius thereof. Next, in the first quadrupole, ions with specific mass number are resonated for selection and other ions are excluded. The selected ions are transferred to the second quadrupole, and cleavage is carried out upon their collision with argon. This reaction is referred to as collision-induced dissociation (CID). The specific fragments that are produced as a result of this cleavage reaction are selected from the third quadrupole, and thus very highly sensitive and highly selective quantification can be achieved. This serial analysis is referred to as multiple reaction monitoring (MRM).

An apparatus that is particularly suitable for the method of the present invention is not particularly limited, but examples thereof include LCMS-8030, LCMS-8040, LCMS-8050, LCMS-8060, and LCMS-8080 (all manufactured by SHIMADZU CORPORATION), LCMS-IT-TOF, and LCMS-Q-TOF (SHIMADZU CORPORATION).

To identify an antibody based on the result of mass spectrometry, existing database can also be utilized. For example, by using Mascot search (Matrix Science) and performing automatically the assignment of parent ion and series of fragment ions assumed from the spectrum information obtained by mass spectrometry, various information can be obtained.

Furthermore, by specifying the amino acid sequence of a peptide fragment by multi-step mass spectrometry, identification of an antibody can be made. If a peptide fragment including an antibody-specific Fab region, for example, a peptide fragment including the amino acid sequence of a heavy chain and/or light chain CDR1 region, CDR2 region, and/or CDR3 region can be detected, a target antibody can be identified and quantified.

Furthermore, for a case in which the identification or quantification of an antibody is carried out based on a detection result, the peptide to be detected preferably has amino acid residue number of 5 to 30, and more preferably 7 to 25. If the number of amino acid residues is excessively small, it is difficult to get distinguished from impurities or a peptide fragment originating from other parts of the same protein, and thus yielding a cause of erroneous detection or the like. On the other hand, if the number of amino acid residues is excessively large, due to the reason like a difficulty for having ionization, the detection may be difficult or the quantification property may be impaired.

When the concentration of an antibody is quantified, the amount of the antibody can be calculated based on the peak areas or peak intensities of detected peptide fragment ions (in the case of multi-step MS, fragment ions obtained by cleavage of parent ion). For example, the concentrations of the peptide fragments in a sample are calculated based on the linking between a previously-determined standard curve (calibration curve) and peak areas, the linking between peak areas derived from an internal standard added to the sample and peak areas derived from the sample, or the like, and the amount or concentration of the antibody is calculated based on the concentration of the peptide fragments.

Furthermore, it is well known that, in mass spectrometry, several kinds of fragment ions are produced for detection of one kind of peptide. When reference is made to analysis results of internal standard peptides or previously-determined analysis results, it is possible to identify a target monoclonal antibody by detecting only one kind of ion from one kind of peptide. However, by simultaneously detecting and quantifying plural fragment ions that are produced from one kind of parent ion, for example, two or more, three or more, or four or more kinds of fragment ions, more detailed structural information can be obtained. However, if the amount of fragment information is excessively large, the analysis time becomes longer, consequently leading to a decrease in analysis precision. As such, it is generally preferable that about two to five kinds of fragment ions are simultaneously monitored for one kind of parent ion. Furthermore, for the fragment ions, it is preferable to select y ion series as an ion series. If there is no such primary candidate, b ion series may be selected. By selecting an ion with the highest ion yield among fragment ions for quantification and others for structural confirmation, structure specificity can be ensured.

For the simultaneous quantification of plural monoclonal antibodies, analysis can be continuously carried out by performing the measurement of each antibody for measurement time in a range of several milliseconds to several tens of milliseconds while switching channels. Accordingly, plural monoclonal antibodies which may be present in a sample can be quantified all together. The detection by mass spectrometry allows rapid and accurate obtainment of information in large amount within a short time. According to the method of the present invention, the antibody which has been previously administered to a certain patient or a subject and the antibody in the process of administration can be collectively and simultaneously quantified.

Furthermore, for carrying out the nSMOL method, the pre-treatment kit for LC/MS/MS "nSMOL Antibody BA Kit" (SHIMADZU CORPORATION) is commercially available. By using it in conjunction with LCMS-8050/8060, for example, quantification of a monoclonal antibody can be easily carried out at high precision•low cost.

<Consideration of Conditions for Analysis>

The amino acid sequence information was available for the monoclonal antibody intended to be used as an antibody pharmaceutical, and it is also possible to obtain the information for the amino acid sequence of a heavy chain and a light chain, Fab and Fc domains, complementarity determining region (CDR), and disulfide bonds. As such, although plural peptides are obtained as a result of the protease digestion by the nSMOL method, once the amino acid sequence information is obtained for each peptide, it is easy to understand that the peptide is present at which location of the monoclonal antibody. Therefore, from the plural peptides originating from Fab region, a particularly preferred peptide can be selected as an analysis subject. Thus-selected peptide is referred to as a "signature peptide."

The monoclonal antibody may include the amino acid sequence that is the same as or similar to that of endogenous antibodies in a human patient, particularly in a constant region. As such, for specific quantification, a method of obtaining peptides by Fab region-selective protease digestion is suitable. However, it is also contemplated that, even a peptide originating from Fab region may have the same or similar sequence to the endogenous antibody or a monoclonal antibody which is another antibody pharmaceutical that may be present in a sample, and is not suitable for detection.

Therefore, as it is commonly performed in the art, it is preferable to confirm the selection of a signature peptide suitable for specific detection by aligning the amino acid sequence of a monoclonal antibody as an analysis target with an amino acid sequence of another monoclonal antibody which may coexist.

For sequence alignment, it is possible to use ClustalW (http://www.ebi.ac.uk/Tools/msa/clustalw2/) which is provided by the European Bioinformatics Institute and the like, and is available on the internet. With ClustalW, it is possible to deduce the CDRs of each monoclonal antibody and obtain the information of a peptide which includes the CDR sequence at least partly and thus is expected to be obtained by protease digestion.

Furthermore, by using Skyline (https://skyline.gs.washington.edu) developed by the group of MacCoss et al. at University of Washington in USA, optimization of the parameters for analysis, for example, a signature peptide and a transition, can be carried out based on the obtained sequence information. In addition, LabSolutions (SHIMADZU CORPORATION) is a system for control, interpretation, and management of data, and information for optimum conditions for MRM analysis can be obtained by importing the obtained information.

By actually carrying out the protease digestion by the nSMOL method and simultaneously using the aforementioned database and system, it becomes possible to obtain more easily the optimum signature peptide for each monoclonal antibody and MRM analysis conditions therefor. Once the optimum signature peptide and the optimum MRM analysis conditions therefor are obtained, it is possible to prepare in advance a calibration curve that can be used for quantification of each monoclonal antibody, and, from the viewpoint that the same validation is obtained from mixed quantification of plural monoclonal antibodies, plural calibration curves that are usable for simultaneous quantification of plural monoclonal antibodies can be also established.

A signature peptide of trastuzumab which can be suitably used for the method of the present invention includes IYPTNGYTR (SEQ ID NO: 1), FTISADTSK (SEQ ID NO: 2), DTYIHWVR (SEQ ID NO: 3), NTAYLQMNSLR (SEQ ID NO: 4) and the like including the amino acid in a heavy chain CDR2 region, for example, although it is not limited thereto. Considering the presence or absence of an interference by human plasma, particularly high correlation with blood concentration, or the like, it is most preferable to use IYPTNGYTR (SEQ ID NO: 1).

In addition, a signature peptide of bevacizumab which can be suitably used for the method of the present invention includes STAYLQMNSLR (SEQ ID NO: 5), FTFSLDTSK (SEQ ID NO: 6), VLIYFTSSLHSGVPSR (SEQ ID NO: 7) and the like, for example. Considering the presence or absence of an interference by human plasma, particularly high correlation with blood concentration, or the like, it is most preferable to use FTFSLDTSK (SEQ ID NO: 6) or VLIYFTSSLHSGVPSR (SEQ ID NO: 7).

The present invention further provides a method for evaluation of effectiveness of a monoclonal antibody administered to a subject, in which the method comprises performing selective protease digestion of a monoclonal antibody by bringing a porous body having the monoclonal antibody in a biological sample derived from the subject immobilized in pores thereof into contact with nanoparticles having the protease immobilized thereonto in a liquid, calculating concentration of the monoclonal antibody in the biological sample by detecting a peptide fragment resulting from the digestion by liquid chromatography mass spectrometry (LC-MS), and determining the presence or absence and/or degree of influence on calculation result exhibited by existence of an antibody specifically binding to the monoclonal antibody.

When a monoclonal antibody is administered as an antibody pharmaceutical to a subject, antibody concentration in living body, for example, blood concentration, increases immediately after the administration like other pharmaceuticals. However, the concentration gradually decreases thereafter. When the administration is made repeatedly, the increase and decrease in concentration is repeated, and, in the case of blood concentration, the maximum value and the minimum value are referred to as a peak value and a trough value, respectively. For effective administration of a pharmaceutical, it is important to have, in addition to the confirmation of clinical effect thereof, comparison between the pharmaceutical concentration after administration with a peak value and a trough value. By employing the method of the present invention, the effectiveness can be evaluated by monitoring the concentration of a monoclonal antibody administered to a subject.

When administering a monoclonal antibody, high blood concentration is achieved because an anti-drug antibody (ADA) against the monoclonal antibody is rarely present immediately after the administration. However, if the administration is continued for a long period of time, an ADA is produced and, according to binding to the administered monoclonal antibody, it can inhibit the pharmaceutical effect. In addition, even when the same monoclonal antibody is administered, type and amount of ADAs which may be produced against the antibody pharmaceutical may vary depending on the state of an immune system of a subject.

Furthermore, in an actual clinical case, it is known that, depending not only on the difference in an immune system of a patient but also on a type of a monoclonal antibody which is selected as an antibody pharmaceutical, there is a case in which an ADA is produced at relatively early stage and the therapeutic effect is significantly inhibited and also a case in which an ADA is hardly produced and the treatment is effective for a long period of time. As such, it is very important to obtain the information regarding whether the administered monoclonal antibody is suitable for the treatment of that patient or not.

However, as described herein, there is a possibility that the measurement value of blood concentration of a monoclonal antibody is affected by an ADA or other factors. This may influence on the determination of treatment results brought by an antibody pharmaceutical. In measurement by an ELISA method, an occurrence of a huge influence on the measurement by the presence of an ADA and a difficulty for carrying out the measurement of actual blood concentration are as described in Examples. In this regard, according to the method of the present invention, by providing an actual blood concentration measurement value of an antibody pharmaceutical, useful information in terms of the effectiveness of a treatment by an antibody pharmaceutical or evaluation of a pharmaceutical effect can be obtained.

Namely, according to the aforementioned method, it is indicated that, when there is no influence or very little influence on a calculation result by the presence of an antibody specifically binding to a monoclonal antibody, the monoclonal antibody is present at therapeutically effective concentration in a biological sample, and thus it is indicated that a treatment using the monoclonal antibody is effective. On the other hand, when there is a huge influence on a calculation result by the presence of an antibody specifically binding to a monoclonal antibody, it is indicated that the amount of the monoclonal antibody is too high, that is, there is an immune system easily responding to the monoclonal antibody, and it is also indicated that a consideration is necessary to see whether or not a treatment by the monoclonal antibody is effective. Furthermore, depending on cases, it may be necessary to increase the dose of the monoclonal antibody or to consider the modification of administration method and/or treatment method, or change of the therapeutic agent.

The presence or absence and/or degree of influence on calculation result can be determined, for example, by obtaining plural ADAs which may appear in a subject and are capable of binding to different epitopes for a specific monoclonal antibody, detecting the monoclonal antibody by the method of the present invention in the presence of the ADAs, and comparing detection results among plural subjects, so that a large amount of information is accumulated for the monoclonal antibody and, depending on a case, the information is compared with a specific detection result which has been detected over time.

In one embodiment of the present invention, the monoclonal antibody is trastuzumab, and, in that case, it is preferable to detect a peptide fragment having the amino acid sequence represented by SEQ ID NO: 1 to 4. In another embodiment, the monoclonal antibody is bevacizumab, and, in that case, it is preferable to detect a peptide fragment having the amino acid sequence represented by SEQ ID NO: 5 to 7.

EXAMPLES

The present invention is described in greater detail in view of the following Examples, but the present invention is not limited by Examples.

Example 1

As an anti-trastuzumab antibody (ADA), HCA168, HCA176, HCA177 (all by Bio-Rad Laboratories, Inc.), and MAB11130 (Abnova Corporation) were used. Immunogens used for the preparation of each ADA, type of ADA, and affinity of ADA for trastuzumab are shown in Table 1.

TABLE 1

| Name of ADA | Immunogen | Format | Affinity (Kd, nM) |
| --- | --- | --- | --- |
| HCA168 | Trastuzumab | Fab-FH2 | 0.02 |
| HCA176 | Trastuzumab | Human IgG1 | 0.4 |
| HCA177 | Trastuzumab | Human IgG1 | 0.02 |
| MAB11130 | F(ab)2 fragment of Trastuzumab | Mouse IgG1 | |

Three formats of the anti-trastuzumab antibody (ADA) shown in Table 1 and trastuzumab (CHUGAI PHARMACEUTICAL CO., LTD.) were allowed to bind to each other according to a reaction at room temperature for 30 minutes in PBS containing 0.1% n-octyl-β-D-thioglucopyranoside (OTG). Binding of the ADA to trastuzumab was confirmed by Western blot.

Human plasma (manufactured by Kohjin Bio Co., Ltd., obtained by filtration using 5 μm filter followed by filtration using 0.8 μm filter) was added in an amount of 10 μL. The sample to be quantified by the nSMOL method was stored at −30° C. until pre-treatment and quantification by the nSMOL method. Concentration of the ADA-bound trastuzumab in plasma was quantified by the ELISA method and the nSMOL method.

For the ELISA method, an ELISA kit (Trastuzumab PK ELISA, Somru BioScience, SBA-100-007-035), in which a trastuzumab specific anti-idiotype monoclonal antibody is used as a capturing reagent and a trastuzumab specific polyclonal antibody is used as a detection reagent is used, was employed.

Procedures of the nSMOL method carried out in this Example are described below. As for the reagents, containers, or the like to be used, those provided in "nSMOL Antibody BA Kit" along with the instructions by SHIMADZU CORPORATION can be used.

Entire suspension is transferred to Ultrafree PVDF (0.2 μm, Merck KGaA), and, by centrifuge for 0.5 to 1 minute at 10,000×g, supernatant is removed. Subsequently, 150 μL of PBS containing 0.1% n-octyl-β-D-thioglucopyranoside (washing solution 1) are added, and washing is carried out by performing the centrifuge two times as described above. Subsequently, 150 μL of PBS (washing solution 2) are added, and washing is carried out by performing the centrifuge two times as described above.

After the washing, the Ultrafree filter cup is transferred to a container that is exclusive for reaction. After pressing it completely to the bottom, 80 µl of reaction accelerating solution and internal standard (10 fmol/µL $P_{14}R$) are added.

Subsequently, 10 µL (0.5 mg/mL trypsin) of FG beads Trypsin DART® (particle diameter: 200 nm) are added, and the reaction is allowed to occur (4 to 6 hours) under mild stirring at 50° C., saturated vapor pressure.

The reaction stop solution (10% aqueous formic acid solution) is added in an amount of 5 µL to terminate the reaction. After that, the supernatant is collected by centrifuge for 0.5 to 1 minute at 10,000×g, and then allowed to stand for approximately 1 minute on a magnetic stand.

The supernatant is transferred to an LCMS vial, and the analysis is carried out. The supernatant contains a peptide derived from Fab region, which was obtained by the selective protease digestion by the nSMOL method.

<LC-MS Analysis Conditions>

Conditions for LC-MS analysis used in this Example are as described below.
[LC] NexeraX2 system (SHIMADZU CORPORATION)
Solvent A: 0.1% formic acid+water
Solvent B: 0.1% formic acid+acetonitrile
Autosampler washing: ultrapure water
Flow rate: 0.4 mL/minute
Column: Shim-pack GISS 2.1×50 mm, 1.9 µm, 20 nm pore
Column oven temperature: 50° C.
Sample cooler temperature: 5° C.
Gradient: 3% B (1.5 minutes)/3 to 30% B (3.5 minutes)/95% B (1 minute)/3% B (1 minute)
Injection amount: 10 µL
[MS] LCMS-8050 (SHIMADZU CORPORATION)
Interface conditions:
Interface voltage: 4 kV
Nebulizer gas flow rate: 3 L/minute
Heating gas flow rate: 10 L/minute
Drying gas flow rate: 10 L/minute
Interface temperature: 300° C.
DL temperature: 250° C.
Heat block temperature: 400° C.

In this Example, as a peptide fragment for quantification of trastuzumab (signature peptide), IYPTNGYTR (SEQ ID NO: 1) present in CDR2 region of a heavy chain was selected. Parent ion and fragment ions of this peptide, and conditions for MRM analysis are shown in Table 2. One of the three fragment ions was used for the quantification, and the two ions were used for structure confir mation.

TABLE 2

Signature peptide of trastuzumab and conditions for MRM analysis

| | | Optimum conditions for MRM | | | |
|---|---|---|---|---|---|
| Peptide | Region | Ion selection [m/z] | Q1 [V] | Collision [V] | Q3 [V] | Purpose |
| IYPTNGYTR (SEQ ID NO: 1) | Heavy chain CDR2 | 542.8→404.7 ($y7^{++}$) | −20 | −18 | −30 | Quantification |
| | | 542.8→808.4 ($y7^{+}$) | −20 | −18 | −28 | Structure determination |
| | | 542.8→610.3 ($y5^{+}$) | −20 | −25 | −22 | Structure determination |

Table 3 shows detection results of the nSMOL method and the ELISA method in which various trastuzumab to ADA ratios are used with trastuzumab concentration of 0.5 µg/mL.

TABLE 3

| Trastuzumab to ADA ratio | HCA168 Accuracy (%) | | HCA176 Accuracy (%) | | HCA177 Accuracy (%) | | MAB11130 Accuracy (%) | |
|---|---|---|---|---|---|---|---|---|
| | nSMOL | ELISA | nSMOL | ELISA | nSMOL | ELISA | nSMOL | ELISA |
| 10:1 | 109 | 95.2 | 106 | 116 | 98.4 | 103 | 105 | 102 |
| 5:1 | 113 | 102 | 93.3 | 98.0 | 98.7 | 112 | 103 | 96.9 |
| 1:1 | 106 | 84.1 | 99.9 | 78.7 | 96.1 | 110 | 102 | 0.632 |
| 1:2 | 102 | 82.1 | 93.4 | 75.2 | 84.4 | 99.9 | 97.8 | ND |
| 1:5 | 93 | 67.7 | 101 | 75.4 | 78.7 | 99.4 | 108 | ND |
| 1:10 | 107 | 62.2 | 89.1 | 76.6 | 81.0 | 108 | 109 | ND |
| 1:50 | 86.0 | 64.5 | 86.6 | 73.1 | 89.5 | 112 | 115 | ND |
| 1:100 | 84.8 | 72.2 | 88.7 | 82.6 | 74.1 | 106 | 100 | ND |

As shown in Table 3, the ELISA method shows a result that quantification values (accuracy) are greatly affected by the presence of any ADA, and that the detection cannot be made when MAB11130 is present more than two times the trastuzumab. However, although the influence on quantification values varies depending on the type of ADAs in the quantification by the nSMOL method, in the presence of any ADA, very high precision is obtained when the trastuzumab to ADA ratio is 1:1 or higher and accuracy of at least 80% was achieved even at the ratio of 1:50. Human IgG (HCA177), which is an anti-idiotype antibody with high affinity, inhibits most the quantification by the nSMOL method, and the antibody against the Fab of trastuzumab (MAB11130) showed no influence on the quantification values of trastuzumab.

Example 2

The result obtained by similar test as Example 1 with trastuzumab concentration of 50 µg/mL is shown in Table 4.

TABLE 4

| Trastuzumab to ADA ratio | HCA168 Accuracy (%) | | HCA176 Accuracy (%) | | HCA177 Accuracy (%) | | MAB11130 Accuracy (%) | |
|---|---|---|---|---|---|---|---|---|
| | nSMOL | ELISA | nSMOL | ELISA | nSMOL | ELISA | nSMOL | ELISA |
| 100:1 | 89.5 | 84.9 | 94.7 | 84.6 | 96.2 | 98.0 | 102 | 83.5 |
| 10:1 | 101.5 | 84.4 | 104.1 | 69.6 | 103.1 | 85.3 | 110 | 74.2 |
| 5:1 | 92.8 | 66.8 | 96.7 | 72.1 | 99.4 | 92.0 | 105 | 72.8 |
| 1:1 | 92.9 | 81.4 | 94.8 | 57.3 | 88.0** | 84.5 | 102 | 2.75 |

**$p < 0.05$

As shown in Table 4, also in a case in which trastuzumab concentration is 50 µg/mL, the ELISA method shows a result that quantification values (accuracy) are greatly affected by the presence of any ADA, while the degree of influence on quantification values varies depending on the type of ADA in the quantification by the nSMOL method. Human IgG (HCA177), which is an anti-idiotype antibody, inhibits most the quantification by the nSMOL method, and the antibody against the Fab of trastuzumab (MAB11130) showed no influence on the quantification values of trastuzumab.

Example 3

Whether or not the orientation of trastuzumab immobilized on Protein A is involved in the influence of ADA on the quantification by the nSMOL method was studied. To align the orientation under all conditions, trastuzumab was immobilized first onto Protein A, and, after binding an ADA to the trastuzumab immobilized onto Protein A, measurement by the nSMOL method was carried out under the conditions described in Example 1. The same ADAs as those in Examples 1 and 2 were used.

To a porous body having particle diameter of 100 nm (TOYOPEARL AF-rProtein A HC-650F resin (manufactured by Tosoh Corporation, 50% slurry, 10 µL) having Protein A, which binds to the Fc domain of IgG in site specific manner, immobilized in pores thereof, trastuzumab (50 µg/mL, 10 µL) was added, and then the reaction was conducted for 10 minutes at room temperature under mild shaking.

Human IgG (1 mg/mL, Cosmo Bio Co., Ltd.) was added in an amount of 400 µg, and then the reaction was conducted for 10 minutes at room temperature under mild shaking.

Unreacted IgG was removed by filtration, and washing was carried out with PBS containing 0.1% OTG.

ADA was added, and then the reaction was conducted for 30 minutes at room temperature under mild shaking.

Concentration of ADA-conjugated trastuzumab was quantified by the nSMOL method. The result is shown in Table 5.

TABLE 5

| Trastuzumab to ADA ratio | HCA168 Accuracy (%) | HCA176 Accuracy (%) | HCA177 Accuracy (%) | MAB11130 Accuracy (%) |
|---|---|---|---|---|
| 100:1 | 107 | 93.5 | 94.7 | 109 |
| 10:1 | 101 | 102 | 103 | 105 |

TABLE 5-continued

| Trastuzumab to ADA ratio | HCA168 Accuracy (%) | HCA176 Accuracy (%) | HCA177 Accuracy (%) | MAB11130 Accuracy (%) |
|---|---|---|---|---|
| 5:1 | 94.3 | 98.3 | 97.3 | 108 |
| 1:1 | 94.5 | 102 | 89.2** | 96.2 |

**$p < 0.05$

When making the orientation of trastuzumab constant, the inhibitory effect on quantification values was about 10% if HCA177 is reacted with trastuzumab at a ratio of 1:1. From this result, it was indicated that the orientation of trastuzumab on Protein A does not control the reaction by the nSMOL method.

Example 4

Detection result by the ELISA method using different kits were studied with trastuzumab concentration of 0.5 µg/mL.

As a kit for ELISA, Kit A (Trastuzumab PK ELISA, Somru BioScience, SBA-100-007-035) in which a trastuzumab specific anti-idiotype monoclonal antibody is used as a capturing reagent and a trastuzumab specific polyclonal antibody is used as a detection reagent, and Kit B (MATRIKS BIOTEK, TR-TRASV1) in which human recombinant HER2 to become a ligand is used as a capturing reagent and an HRP-conjugated anti-human IgG Fc monoclonal antibody is used as a detection reagent is used were employed. As shown in Table 6, it was evident that a difference in quantification values of ADA-conjugated trastuzumab occurs depending on the type of ELISA kit.

TABLE 6

| Trastuzumab to ADA ratio | HCA168 Accuracy (%) | | HCA176 Accuracy (%) | | HCA177 Accuracy (%) | | MAB11130 Accuracy (%) | |
|---|---|---|---|---|---|---|---|---|
| | Kit A | Kit B | Kit A | Kit B | Kit A | Kit B | Kit A | Kit B |
| 10:1 | 95.2 | 95.5 | 116 | 101 | 103 | 97.4 | 102 | 88.9 |
| 1:1 | 84.1 | 42.4 | 78.7 | 36.1 | 110 | 46.0 | 0.632 | 3.69 |
| 1:10 | 62.2 | 6.40 | 76.6 | 3.93 | 108 | 0.962 | ND | 1.36 |
| 1:100 | 72.2 | 3.32 | 82.6 | 11.7 | 106 | ND | ND | 4.49 |

Example 5

Influence on the detection result in the presence of HER2 as a target molecule was studied with trastuzumab concentration of 0.5 μg/mL.

Human recombinant HER2 (Funakoshi Co., Ltd.) and trastuzumab (CHUGAI PHARMACEUTICAL CO., LTD.) were allowed to bind to each other by the reaction at room temperature for 30 minutes in PBS containing 0.1% OTG. Binding of HER2 to trastuzumab was confirmed by Western blot.

Human plasma (manufactured by Kohjin Bio Co., Ltd., obtained by filtration using 5 μm filter followed by filtration using 0.8 μm filter) was added in an amount of 10 μL. The sample to be quantified by the nSMOL method was stored at −30° C. until pre-treatment and quantification by the nSMOL method.

Concentration of HER2-conjugated trastuzumab in plasma was quantified by the ELISA method and the nSMOL method under conditions described in Example 1.

As a result, as shown in Table 7, there was almost no influence on the detection result by the nSMOL method, even when the HER2 is present in an amount 100 times more than trastuzumab. On the other hand, according to the ELISA method, the detection result was greatly affected depending on the amount of HER2.

TABLE 7

| Trastuzumab to HER2 ratio | Trastuzumab (0.5 μg/mL) Accuracy (%) | |
|---|---|---|
| | nSMOL | ELISA |
| 10:1 | 114 | 98.7 |
| 5:1 | 103 | 96.4 |
| 1:1 | 102 | 54.6 |
| 1:5 | 91.4 | 1.4 |
| 1:10 | 95.9 | 1.1 |

TABLE 7-continued

| Trastuzumab to HER2 ratio | Trastuzumab (0.5 μg/mL) Accuracy (%) | |
|---|---|---|
| | nSMOL | ELISA |
| 1:50 | 98.7 | 0.7 |
| 1:100 | 108 | 0.4 |

Example 6

As an anti-bevacizumab antibody (ADA), HCA182, HCA185, HCA177 (all by Bio-Rad Laboratories, Inc.), and MAB11128 (clone2C8, Abnova Corporation) were used. Immunogens used for the preparation of each ADA, format of ADA, and affinity of ADA for bevacizumab are shown in Table 8.

TABLE 8

| ADA name | Immunogen | Format | Affinity (Kd, nM) |
|---|---|---|---|
| HCA185 | Bevacizumab | Human IgG1 | 0.4 |
| HCA182 | Bevacizumab | Human Fab | 0.4 |
| MAB11128 | F(ab)2 fragment of Bevacizumab | Mouse IgG1 | |

In this Example, as a peptide fragment for quantification of bevacizumab (signature peptide), FTFSLDTSK (SEQ ID NO: 6) present in CDR2 region of a heavy chain was selected. Parent ion and fragment ions of this peptide, and conditions for MRM analysis are shown in Table 9. One of the three fragment ions was used for the quantification, and the two ions were used for structure confirmation. The LC-MS analysis conditions used for this Example were the same as those in Example 1 except that the interface voltage is set at 1.5 kV and interface temperature is set at 350° C.

TABLE 9

Signature peptide of bevacizumab and conditions for MRM analysis

| Peptide | Region | Optimum conditions for MRM | | | |
|---|---|---|---|---|---|
| | | Ion selection [m/z] | Q1 [V] | Collision [V] | Q3 [V] | Purpose |
| FTFSLDTSK (SEQ ID NO: 6) | Heavy chain CDR2 | 523.3→797.4 (y7+) | −17 | −18 | −30 | Quantification |
| | | 523.3→898.5 (y8+) | −17 | −20 | −34 | Structure determination |
| | | 523.3→650.3 (y6+) | −17 | −19 | −34 | Structure determination |

As an ELISA kit, Bevacizumab PK ELISA (Somru BioScience, SBA-100-007-041), in which bevacizumab specific anti-idiotype monoclonal antibody is used as a capturing antibody and bevacizumab specific polyclonal antibody is used as a detection antibody, used was employed.

Table 10 shows accuracy (%) for detection results by the nSMOL method and the ELISA method in which the anti-bevacizumab antibody is used at various ratios to bevacizumab concentration of 0.5 µg/mL.

TABLE 10

| Bevacizumab to ADA ratio | HCA185 Accuracy (%) | | HCA182 Accuracy (%) | | MAB11128 Accuracy (%) | |
|---|---|---|---|---|---|---|
| | nSMOL | ELISA | nSMOL | ELISA | nSMOL | ELISA |
| 10:1 | 107 | 104 | 100 | 108 | 91.3 | 44.2 |
| 5:1 | 105 | 86.6 | 102 | 95.8 | 98.0 | 14.2 |
| 1:1 | 95.5 | 73.5 | 87.7 | 77.0 | 98.2 | 6.9 |
| 1:2 | 82.1** | 55.8 | 75.3** | 54.3 | 110 | 3.2 |
| 1:5 | 54.8** | 39.6 | 55.1** | 33.5 | 111 | 2.3 |
| 1:10 | 22.8** | 38.9 | 58.4** | 36.5 | 110 | 2.4 |
| 1:50 | 22.9** | 37.2 | 55.7** | 36.1 | 110 | 0.1 |
| 1:100 | 23.1** | 35.2 | 52.2** | 38.4 | 104 | 0.0 |

**$p < 0.05$

In the ELISA method, there was an influence on the quantification values by any type of ADAs used for the study (accuracy is −5 to −100%). However, in the quantification by the nSMOL method, the degree of influence on quantification values was different depending on the type of ADA. Human IgG (HCA185), which is an anti-idiotype antibody, inhibits most the quantification by the nSMOL method, and the antibody against the Fab of bevacizumab (MAB11128) showed no influence on the quantification values of bevacizumab.

Example 7

Results obtained by similar test as Example 6 with bevacizumab concentration of 50 µg/mL are shown in Table 11.

TABLE 11

| Bevacizumab to ADA ratio | HCA185 Accuracy (%) | | HCA182 Accuracy (%) | | MAB11128 Accuracy (%) | |
|---|---|---|---|---|---|---|
| | nSMOL | ELISA | nSMOL | ELISA | nSMOL | ELISA |
| 100:1 | 100 | 95.6 | 99.8 | 91.1 | 101 | 101.8 |
| 10:1 | 95.8 | 84.1 | 96.6 | 80.4 | 100 | 68.5 |
| 5:1 | 90.3 | 76.2 | 89.3 | 61.8 | 97.3 | 65.5 |
| 1:1 | 75.7 | 76.8 | 75.4 | 59.2 | 102 | 5.72 |

In the ELISA method, there was an influence on the quantification values by any type of the ADA used for the study (accuracy is −5 to −95%). However, in the quantification by the nSMOL method, the degree of influence on quantification values was different depending on the type of ADA. Human IgG (HCA185), which is an anti-idiotype antibody, inhibits most the quantification by the nSMOL method, and the antibody against the Fab of bevacizumab (MAB11128) showed no influence on the quantification values of bevacizumab.

Example 8

Whether or not the orientation of bevacizumab immobilized on Protein A is involved in the influence of ADA on the quantification by the nSMOL method was studied. To align the orientation under all conditions, bevacizumab was immobilized first onto Protein A, and, after binding an ADA to the bevacizumab immobilized onto Protein A, measurement by the nSMOL method was carried out. The same ADAs as those in Examples 6 and 7 were used.

TABLE 12

| Bevacizumab to ADA ratio | HCA185 Accuracy (%) | HCA182 Accuracy (%) | MAB11128 Accuracy (%) |
|---|---|---|---|
| 100:1 | 105 | 104 | 109 |
| 10:1 | 106 | 106 | 104 |
| 5:1 | 90.0** | 104 | 106 |
| 1:1 | 58.9** | 70.4** | 106 |

**$p < 0.05$

As shown in Table 12, when making the orientation of bevacizumab constant, the inhibitory effect on quantification values was about 50% if HCA185 is reacted with bevacizumab at a ratio of 1:1. This result suggests that the anti-idiotype antibody against bevacizumab binds to one Fv region of bevacizumab instead of both sides of the bevacizumab dimer, and inhibits the enzyme digestion reaction by trypsin.

Example 9

The influence on detection result in the presence of VEGF as a target molecule with bevacizumab concentration of 0.5 µg/mL was studied.

Human recombinant VEGF (223-01311, FUJIFILM Wako Pure Chemical Corporation) and bevacizumab (CHUGAI PHARMACEUTICAL CO., LTD.) were allowed to bind to each other in the reaction at room temperature for 30 minutes in PBS containing 0.1% OTG. Binding of VEGF to bevacizumab was confirmed by Western blot.

Human plasma (manufactured by Kohjin Bio Co., Ltd., obtained by filtration using 5 µm filter followed by filtration using 0.8 µm filter) was added in an amount of 10 µL. The sample to be quantified by the nSMOL method was stored at −30° C. until pre-treatment and quantification by the nSMOL method.

Concentration of VEGF-conjugated bevacizumab in plasma was quantified in the same manner as Example 6 by the ELISA method and the nSMOL method.

As a result, as shown in Table 13, there was almost no influence on the detection result by the nSMOL method, even when VEGF is present in an amount 100 times more than bevacizumab. On the other hand, in the ELISA method, the detection result was greatly affected depending on the amount of VEGF.

TABLE 13

| Bevacizumab to VEGF ratio | Bevacizumab (0.5 µg/mL) Accuracy (%) | |
|---|---|---|
| | nSMOL | ELISA |
| 10:1 | 100 | 88.4 |
| 5:1 | 101 | 70.9 |
| 1:1 | 102 | 13.3 |
| 1:2 | 97.6 | 4.5 |
| 1:5 | 95.7 | 3.9 |
| 1:10 | 94.5 | 4.2 |
| 1:50 | 96.2 | 4.1 |
| 1:100 | 100 | 2.9 |

Example 10

VEGF and bevacizumab were reacted in equal quantities and accuracy of the quantification values at each concentration of bevacizumab was studied by the nSMOL method under similar conditions as those in Example 9. As a result, as shown in Table 14, with regard to the quantification of bevacizumab by the nSMOL method, VEGF binding exhibits no influence on any concentration within the calibration curve range.

TABLE 14

| Bevacizumab (µg/mL) | VEGF (1:1) Accuracy (%) | |
| --- | --- | --- |
|  | None | VEGF |
| 0.3 | 102 | 107 |
| 3 | 94 | 114 |
| 30 | 105 | 109 |
| 300 | 100 | 111 |

INDUSTRIAL APPLICABILITY

By the method of the present invention, accurate blood concentration of an antibody pharmaceutical can be detected, and useful information in terms of the effectiveness of the treatment by an antibody pharmaceutical or the evaluation of pharmaceutical effects can be provided.

All publications, patents, and patent applications cited in the present specification are incorporated herein by reference in their entirety.

The invention claimed is:

1. A method for evaluation of effectiveness of a monoclonal antibody as an antibody pharmaceutical administered to a subject, comprising:
performing selective protease digestion of a monoclonal antibody by bringing a porous body having the monoclonal antibody immobilized in pores thereof into contact with nanoparticles having the protease immobilized thereonto in a liquid, the monoclonal antibody being from a biological sample from the subject;
calculating concentration of the monoclonal antibody in the biological sample by detecting a peptide fragment resulting from the digestion by liquid chromatography mass spectrometry (LC-MS); and
determining, based on the calculated concentration of the monoclonal antibody, the presence or absence and/or degree of influence on calculation result exhibited by existence of an antibody specifically binding to the monoclonal antibody.

2. The method according to claim 1, wherein the monoclonal antibody is trastuzumab and wherein a peptide fragment having the amino acid sequence represented by any one selected from the group consisting of SEQ ID NO: 1 to 4 is detected.

3. The method according to claim 1, wherein the monoclonal antibody is bevacizumab and wherein a peptide fragment having the amino acid sequence represented by any one selected from the group consisting of SEQ ID NO: 5 to 7 is detected.

4. A method comprising:
administering a monoclonal antibody as an antibody pharmaceutical to a subject;
performing selective protease digestion of a monoclonal antibody by bringing a porous body having the monoclonal antibody immobilized in pores thereof into contact with nanoparticles having the protease immobilized thereonto in a liquid, the monoclonal antibody being from a biological sample from the subject;
calculating concentration of the monoclonal antibody in the biological sample by detecting a peptide fragment resulting from the digestion by liquid chromatography mass spectrometry (LC-MS);
determining, based on the calculated concentration of the monoclonal antibody, the presence or absence and/or degree of influence on calculation result exhibited by existence of an antibody specifically binding to the monoclonal antibody;
evaluating, based on the determined presence or absence and/or degree of influence, effectiveness of the monoclonal antibody administered to a subject; and
considering, based on the evaluated effectiveness, modification of a dose of the monoclonal antibody to the test subject, modification administration method or treatment method, and/or change of a therapeutic agent.

5. The method according to claim 1, wherein the monoclonal antibody is trastuzumab and wherein peptide fragments having the amino acid sequences represented by SEQ ID NO: 1 to 4 are detected.

6. The method according to claim 1, wherein the monoclonal antibody is bevacizumab and wherein peptide fragments having the amino acid sequences represented by SEQ ID NO: 5 to 7 are detected.

7. The method according to claim 4, wherein the monoclonal antibody is trastuzumab and wherein a peptide fragment having the amino acid sequence represented by any one selected from the group consisting of SEQ ID NO: 1 to 4 is detected.

8. The method according to claim 4, wherein the monoclonal antibody is bevacizumab and wherein a peptide fragment having the amino acid sequence represented by any one selected from the group consisting of SEQ ID NO: 5 to 7 is detected.

9. The method according to claim 4, wherein the monoclonal antibody is trastuzumab and wherein peptide fragments having the amino acid sequences represented by SEQ ID NO: 1 to 4 are detected.

10. The method according to claim 4, wherein the monoclonal antibody is bevacizumab and wherein peptide fragments having the amino acid sequences represented by SEQ ID NO: 5 to 7 are detected.

11. The method according to claim 1, wherein the monoclonal antibody is any one selected from the group consisting of panitumumab, ofatumumab, golimumab, ipilimumab, nivolumab, ramucirumab, adalimubab, tocilizumab, trastuzumab, trastuzumab-DM1, bevacizumab, omalizumab, mepolizumab, gemtuzumab, palivizumab, ranivizumab, certolizumab, ocrelizumab, mogamulizumab, eculizumab, rituximab, cetuximab, infliximab, and basiliximab.

12. The method according to claim 4, wherein the monoclonal antibody is any one selected from the group consisting of panitumumab, ofatumumab, golimumab, ipilimumab, nivolumab, ramucirumab, adalimubab, tocilizumab, trastuzumab, trastuzumab-DM1, bevacizumab, omalizumab, mepolizumab, gemtuzumab, palivizumab, ranivizumab, certolizumab, ocrelizumab, mogamulizumab, eculizumab, rituximab, cetuximab, infliximab, and basiliximab.

13. The method according to claim 5, wherein the antibody specifically binding to trastuzumab is an anti-idiotype antibody.

14. The method according to claim 6, wherein the antibody specifically binding to bevacizumab can be an anti-idiotype antibody.

15. The method according to claim 9, wherein the antibody specifically binding to trastuzumab is an anti-idiotype antibody.

16. The method according to claim 10, wherein the antibody specifically binding to bevacizumab is an anti-idiotype antibody.

17. The method according to claim 1, wherein the antibody specifically binding to trastuzumab is an anti-idiotype antibody.

18. The method according to claim 2, wherein the antibody specifically binding to bevacizumab is an anti-idiotype antibody.

19. The method according to claim 7 wherein the antibody specifically binding to trastuzumab is an anti-idiotype antibody.

20. The method according to claim 8, wherein the antibody specifically binding to bevacizumab is an anti-idiotype antibody.

\* \* \* \* \*